(12) United States Patent
Pritchard et al.

(10) Patent No.: US 7,818,132 B2
(45) Date of Patent: Oct. 19, 2010

(54) TEST SYSTEM

(75) Inventors: G. John Pritchard, Cambridge (GB); John J. Rippeth, Ipswich (GB); Nicholas Young Kent, Sandhurst (GB)

(73) Assignee: Arkray Factory Ltd., Woodbridge (GB)

( * ) Notice: Subject to any disclaimer, the term of this patent is extended or adjusted under 35 U.S.C. 154(b) by 273 days.

(21) Appl. No.: 11/921,882

(22) PCT Filed: Jun. 1, 2006

(86) PCT No.: PCT/GB2006/001990

§ 371 (c)(1),
(2), (4) Date: Dec. 7, 2007

(87) PCT Pub. No.: WO2006/131697

PCT Pub. Date: Dec. 14, 2006

(65) Prior Publication Data

US 2009/0119024 A1    May 7, 2009

Related U.S. Application Data

(60) Provisional application No. 60/689,957, filed on Jun. 13, 2005.

(30) Foreign Application Priority Data

Jun. 10, 2005    (GB) .................................. 0511819.5

(51) Int. Cl.
*G01N 33/50* (2006.01)

(52) U.S. Cl. .................... 702/23; 600/365; 600/309; 340/572.1; 422/68.1; 73/864.91; 73/61.48; 73/61.71; 73/64.56; 235/472.01

(58) Field of Classification Search .................. 702/23; 600/365, 309; 340/572.1; 422/68.1; 73/864.91, 73/61.48, 61.71, 64.56; 235/472.01
See application file for complete search history.

(56) References Cited

U.S. PATENT DOCUMENTS 5,628,890 A    5/1997    Carter et al.

(Continued)

FOREIGN PATENT DOCUMENTS

| DE | 10237602 A1 | 3/2004 |
|---|---|---|
| WO | WO97/29847 A1 | 8/1997 |
| WO | WO02/41237 A1 | 5/2002 |

OTHER PUBLICATIONS

Search Report, PCT/GB2006/001990, Nov. 29, 2006, 3 pgs.
Tang et al., "Effects Of Different Hematocrit Levels On Glucose Measurements With Handheld Meters for Point-Of-Care Testing", XP-002407374, Arch Pathol Lab Med, vol. 124, Aug. 2000, 6 pgs.

*Primary Examiner*—Carol S Tsai
(74) *Attorney, Agent, or Firm*—Morgan Lewis & Bockius LLP

(57) ABSTRACT

A test system for measuring the concentration of an analyte in a biological fluid sample comprises: a plurality of test members (16) in a container (10), each test member (16) including reagent means for indicating the catalytic activity of an enzyme when in the presence of a biological fluid containing an analyte acted upon by the enzyme; 0 a test meter (2) for receiving a test member (16), the meter (2) having circuitry for performing a measurement on a test member received therein to produce a measured physical value, means for determining an analyte concentration value for a specified biological fluid from said measured physical value, and means (4) for indicating a determined analyte concentration value; a Container RFID tag (14) associated with the container (10) which includes data specific to said plurality of test members (16); and a Patient RFID tag (28) which includes data specific to a patient; and wherein said test meter (2) includes means for reading and storing data from said Container RFID tag (14) and from said Patient RFID tag (28).

13 Claims, 2 Drawing Sheets

U.S. PATENT DOCUMENTS

| | | | |
|---|---|---|---|
| 5,989,917 A * | 11/1999 | McAleer et al. | 436/46 |
| 7,077,328 B2 * | 7/2006 | Krishnaswamy et al. | 235/472.01 |
| 7,178,416 B2 * | 2/2007 | Whelan et al. | 73/864.91 |
| 2002/0060247 A1 * | 5/2002 | Krishnaswamy et al. | 235/472.01 |
| 2003/0077596 A1 * | 4/2003 | Sundrehagen | 435/6 |
| 2004/0193453 A1 * | 9/2004 | Butterfield et al. | 705/2 |
| 2005/0009122 A1 * | 1/2005 | Whelan et al. | 435/7.32 |
| 2005/0242177 A1 * | 11/2005 | Roberge et al. | 235/383 |
| 2006/0290496 A1 * | 12/2006 | Peeters | 340/572.1 |
| 2008/0114228 A1 * | 5/2008 | McCluskey et al. | 600/365 |
| 2009/0178937 A1 * | 7/2009 | Taylor | 205/792 |

* cited by examiner

TEST SYSTEM

This application claims priority to U.S. provisional application Ser. No. 60/689,957 filed on Jun. 13, 2005. This application also claims priority to GB0511819.5 filed on Jun. 10, 2005.

BACKGROUND OF THE INVENTION

1. Field of the Invention

The present invention relates to a test system, notably to a test system for measuring the concentration of an analyte in a biological fluid, and to a method of using the system. The system is particularly for use in long term care facilities but could also be used in other environments.

2. Description of the Prior Art

In long term care facilities such as hospitals, clinics, care homes, Infirmaries and hospices, it is frequently necessary to monitor the level of analytes such as glucose or cholesterol in a patients body to ensure that the patient is given appropriate food and/or medication. Typically, the analyte concentration is measured in a biological fluid such as a sample of the patients whole blood or urine, using a suitably-calibrated test meter. The test meter typically uses disposable test strips which contain an enzyme reagent system which is specific to a particular analyte and which produces a measurable change in reflectance or an electrochemical value such as electric current. The magnitude of the change or measured value is related to the analyte concentration in the sample. To allow a single meter to be used with different batches of test strips, each batch of test strips may be provided with a code chip which contains batch-specific calibration data. The operator (typically a physician, nurse or care assistant) inserts the code chip in the meter when a new batch of test strips is opened. Any previous code chip is discarded. The meter reads the calibration data (typically contained in a lookup table) and outputs a calibrated analyte concentration value derived from those data and the measured change or value caused by the addition of the fluid sample to the test strip.

The same meter may be used to measure different types of analyte depending on the type of test strip which it is used with. For example, one type of test strip may be used to measure blood glucose and another to measure blood cholesterol. The information about the type of test strip may be encoded in the code chip or may be entered manually by the operator.

It has been proposed in U.S. Pat. No. 5,989,917 to include in a test meter a receptacle for receiving a container of test strips, and a mechanism for reading Information about the test strips that is affixed to the container. The information may be applied to the container in the form of a machine-readable bar-code, magnetic stripe; a memory chip or as a resonant wire loop. A problem with this approach is that the meter is made bulkier by needing to accommodate the container, and switching between measuring one type of analyte and another is time consuming because of the need to remove one container and Insert another. The system also requires that the containers are of a standard size and shape, so that the meter may not be usable with all test strips.

In US 2005/0009122 A1 it is proposed to provide a test cartridge including a test medium and an RFID device that is readable by the meter and contains information useful in controlling the performance of an analyte concentration test. The cartridge may be multi-use (reusable) or single-use (disposable). Where the test cartridge is disposable (as a test strip is) incorporation of an RFID device significantly increases the manufacturing costs of a batch of test strips.

After taking an analyte measurement, the result must be logged on a computer system, together with patient-specific data such as the patient's name. Desirably, other data are also logged to provide a complete medical record trail. Such other data include the Identity of the operator, and the date and time of testing. The computer system may be interrogated by a physician or other personnel when formulating a suitable care regime for the patient.

A problem with existing systems is that recording of the various data can be time consuming, and transcription errors can lead to wrongful diagnoses or sub-optimal care regimes being instituted.

SUMMARY OF THE INVENTION

According to a first aspect of the present invention there is provided a test system for measuring the concentration of an analyte in a biological fluid sample, the system comprising:

a plurality of test members in a container, each test member including reagent means for indicating the catalytic activity of an enzyme when in the presence of a biological fluid containing an analyte acted upon by the enzyme;

a test meter for receiving a test member, the meter having circuitry for performing a measurement on a test member received therein to produce a measured physical value, means for determining an analyte concentration value for a specified biological fluid from said measured physical value, and means for indicating a determined analyte concentration value;

a Container RFID tag associated with the container which includes data specific to said plurality of test members; and a Patient RFID tag which includes data specific to a patient; and wherein said test meter includes means for reading and storing data from said Container RFID tag and from said Patient RFID tag.

The invention allows date pertaining to both the test members and the patent to be input quickly and easily to the meter without manual date entry, thereby reducing the likelihood of transcription errors and the time needed for data entry. If a different analyte test is to be carried out, a different container containing the appropriate test members will be used and the relevant Container RFID data read by the meter. The invention may be used with a container of any shape and size. If different types of testing are required in different wards of a care facility, a single meter may be taken from one ward to another leaving the container with its test members in the ward where it belongs, and using test members already located in the other ward, thereby reducing the likelihood of errors resulting from use of the wrong test members.

The data readable from the Container RFID tag will typically include batch calibration data for the batch of test members. Other data which may be read from the Container RFID tag include: the lot number, the date of manufacture of the test members, the shelf life of the test members (for both closed container and open container conditions), and an open-date or expiry-date deadline. Further data which may optionally be readable from the Container RFID tag include parameter values for modifying operation of the test meter, for example: timing intervals, current thresholds, transient detection filters, and other physical values. Information as to the nature of the analyte to be tested may also be included Prior to taking an analyte reading using a test member, the operator touches the meter against (or brings the meter sufficiently close to) the container for the meter to read and store the Container RFID tag data. The meter may provide visual and/or audible feedback to indicate that is has successfully read the data. The meter may also be programmed not to operate until the data have been input within a pre-set period of time, to reduce the likelihood of error if the meter is swiped over a Container RFID tag for a flat container but a reading not immediately taken, followed later by a test member being taken from a second container.

This aspect of the Invention provides a simple way of providing to the meter batch-specific data and other data relating to the test members. It requires only a single Container RFID tag, which may be included inside the container, optionally adhered to an inner surface, or adhered to the outside of the container or to its lid. Alternatively, the Container RFID tag may be secured to the container by tying, welding or other suitable means. The construction, manufacture and use of the test members may be entirely unchanged from prior art test members.

The test meter may measure optical reflectance or an electrochemical value such as potential, resistivity or current. For convenience herein, the invention will be described with reference to a system which measures blood glucose concentration by amperometry. Each test member will typically comprise a test strip, and the term 'test strip' will be used herein for convenience.

The Patient RFID tag contains patient-specific data, notably the identity of the patent, and will be associated with the patient to whom the data relate. The Patient RFID tag will typically be provided on a carrier which may be affixed to or worn by the patient. For example, the carrier may comprise a bracelet or a neck pendant, or an adhesive material for releasably adhering to the patient's skin or clothing. Alternatively, the carrier may comprise a badge or clip which may be releasably secured to the patients clothing. In an alternative embodiment, the Patient RFID tag may be affixed to or otherwise associated with the patients records; however it is preferred that the Patient RFID tag be provided on the patient or the patient's clothing to reduce the likelihood of error in data entry. The Patient RFID tag is touched against or brought sufficiently close to the meter for the meter to read and store the Patient RFID tag data. This is preferably done before the analyte measurement is made, although it would also be possible for this step to be carried out subsequent to the analyte measurement.

In a preferred embodiment the system further comprises an Operator RFID tag which contains operator-specific data, notably the identity of the operator, and which will be associated with the operator to whom the data relate. The Operator RFID tag will typically be provided on a carrier which may be affixed to or worn by the operator. For example, the carrier may comprise a bracelet or a neck pendant, or an adhesive material for releasably adhering to the operator's skin or clothing. Alternatively, the carrier may comprise a badge or clip which may be releasably secured to the operator's clothing.

The meter may be programmed to require input from either or both of the Patient RFID tag and the Operator RFID tag, optionally within a pre-set time period before an analyte reading is taken.

The meter may be programmed with the date and time, and it may be programmed to check that a test strip is not being used beyond its shelf life. Additionally, or alternatively, the meter may check what time has elapsed since the date when a particular container RFID was first entered on the meter (the 'open' date). If the elapsed time exceeds the open container shelf life, the meter may trigger an alarm condition to warn the operator to discard the test strips and use a new batch.

All of the data and results stored on the meter (including patient and/or operator RFID data) may be uploaded onto a computer system via a suitable reader. Communication with the reader may be by any convenient means and data transfer protocol, for example RF, Infrared, or via a conventional cable. In a preferred embodiment, the data and results are transmitted when the meter is placed on the reader, either automatically or by the operator manually initiating in data transfer.

The term "RFID tag" is used herein to refer to a small RFID device capable of transmitting data by RF and which can be attached to or incorporated into an article. Each RFID tag may be active or passive. In a preferred embodiment, each RFID tag is passive and has a limited range, preferably less than 10 cm, notably less than 5 cm, so that the meter must be brought quite close to the tag to upload its data. Limited range passive tags are of low cost and do not require a power source other than that supplied by the interrogating RF signal from the meter. By limiting the range, the likelihood of a false reading from a similar but more remote RFID tag may be eliminated or greatly reduced. Typically each RFID tag will comprise a microchip attached to an antenna and may comprise a design known per se to those skilled in the art of RFID tag technology.

The test meter may optionally be used with the Patient RFID tag alone, with test strip batch calibration information being provided by conventional means, for example a code chip which accompanies the container. Accordingly, another aspect of the invention provides a test system for measuring the concentration of an analyte in a biological fluid sample, the system comprising:

a plurality of test members in a container, each test member including reagent means for indicating the catalytic activity of an enzyme when in the presence of a biological fluid containing an analyte acted upon by the enzyme;

a test meter for receiving a test member, the meter having circuitry for performing a measurement on a test member received therein to produce a measured physical value, means for determining an analyte concentration value for a specified biological fluid from said measured physical value, and means for indicating a determined analyte concentration value; and a Patient RFID tag which includes data specific to a patient, and wherein said test meter includes means for reading and storing data from said Patient REID tag.

In another aspect of the Invention, the test meter may be used with the Container RFID tag alone, with data specific to a patient and/or an operator being provided by conventional means, for example by keying the data in to the meter. Accordingly, another aspect of the invention provides a test system for measuring the concentration of an analyte in a biological fluid sample, the system comprising:

a container for a plurality of members;

a plurality of test members in the container, each test member including reagent means for indicating the catalytic activity of an enzyme when in the presence of a biological fluid containing an analyte acted upon by the enzyme; and a test meter for receiving a test member but not the container, the meter having circuitry for performing a measurement on a test member received therein to produce a measured physical value, means for determining an analyte concentration value for a specified biological fluid from the measured physical value, and means for indicating a determined analyte concentration value;

wherein the container is provided with a Container RFID tag which includes data specific to the plurality of test members, and wherein the test meter includes means for reading and storing data from the Container RFID tag.

Other aspects and benefits of the Invention will appear in the following specification, drawings and claims.

BRIEF DESCRIPTION OF THE DRAWINGS

The invention will now be further described, by way of example, with reference to the following drawings, in which.

DETAILED DESCRIPTION

Figure 1:
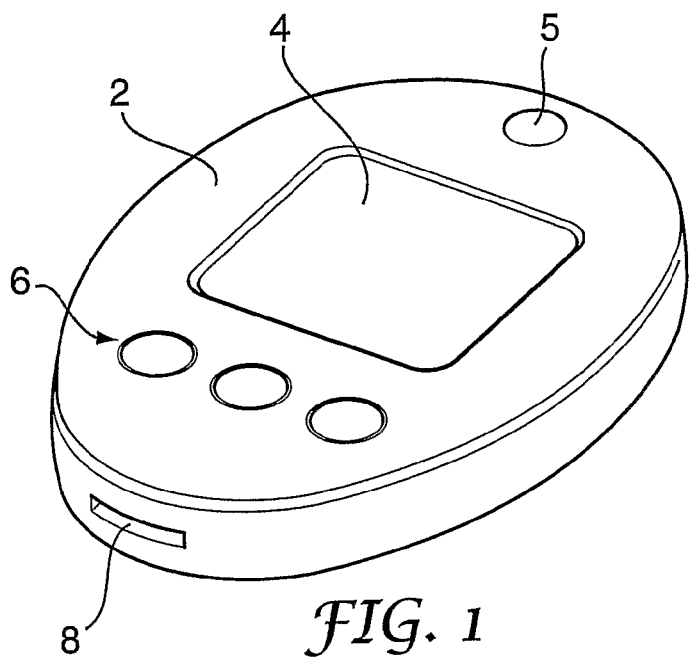
FIG. 1 is a test meter for use in a test system in accordance with the present invention.
Figure 2:
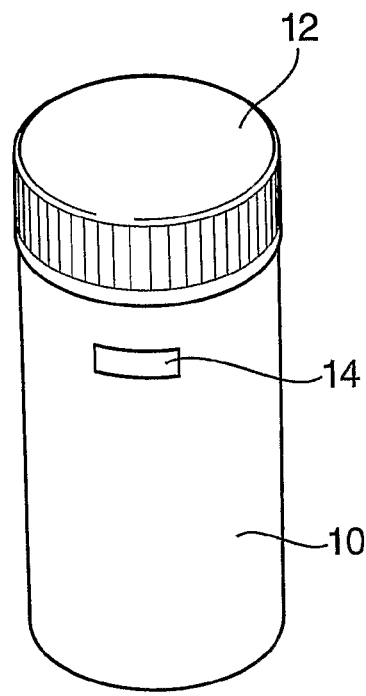
FIG. 2 is a container if test strips for use in a test system in accordance with the present invention.
Figure 3:
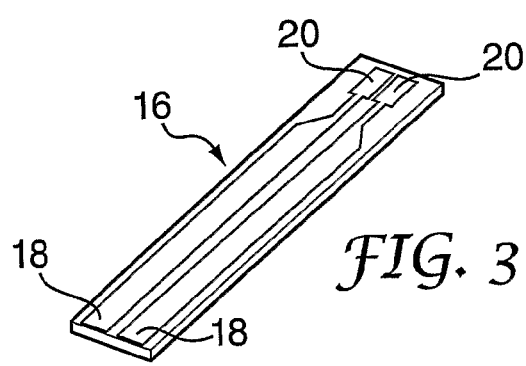
FIG. 3 is a test strip for use with the meter of FIG. 1.

The test meter 2 is a hand-held blood glucose meter of conventional external appearance. The meter 2 has a graphic LCD interface 4 which is capable of displaying information and prompting user actions. Buttons 6 are provided for functions such as ON/OFF, and for scrolling and menu selection. A slot 8 is provided for receiving a test strip 16.

The test strip 16 is a conventional amperometric biosensor which has electrode contacts 18 at one end, for making electrical contact with corresponding contacts within the meter 2, and electrodes 20 at the other end, to which a blood sample will be applied. At least one of the electrodes 20 has an enzyme reagent for generating an electric current in the presence of glucose. The magnitude of the generated current will be indicative of the blood glucose concentration, in a manner well known per se.

A plurality of single-use disposable test strips 16 (for example 50 strips), from a single batch, is provided in a container 10 which is initially factory-sealed. The container 10 has a cap 12 and a Container RFID tag 14 which in this example is adhered to an outer surface of the container 10. The Container RFID tag in this example contains data specific to the batch, including: lot number, date of manufacture, calibration data, shelf life (open container and closed container) and open-date and expiry-date deadlines.

Figure 4:
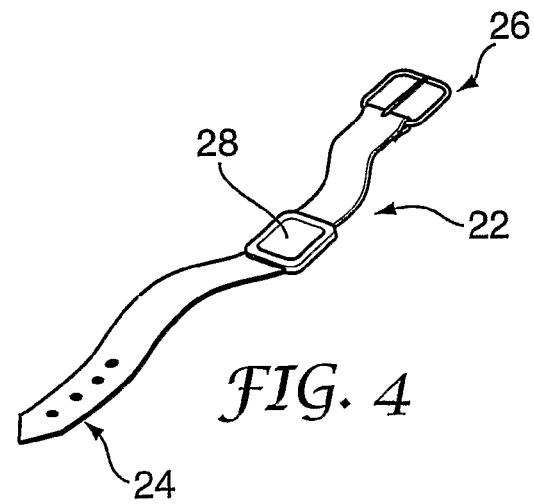
FIG. 4 is a carrier for a Patient RFID tag for use in an embodiment of the present invention.

The carrier 22 shown in FIG. 4, is in the form of a wrist strap, having a holed free end 24 which can be engaged by a buckle 26 for fastening about a person's wrist, in this example the wrist of a patient. The wrist strap 22 carries an RFID tag 28 which in this example is a Patient RFID tag containing data specific to the patient who will wear it. The data include the name or Identification number of the patient.

Figure 5:
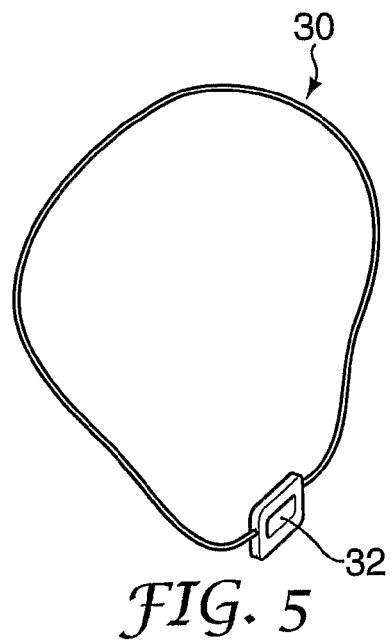
FIG. 5 is an carrier for an Operator RFID tag for use in an embodiment of the present invention.

Turning now to FIG. 5, an alternative carrier is shown, in the form of a necklace 30. The necklace carries an RFID tag 32 which in this example is an Operator RFID tag containing data specific to the operator who will wear it. The data Include the name or identification number of the operator who will use the meter 2. It will be understood that the functions of the Patient RFID tag 28 and the Operator RFID tag 32 could be reversed, or that either could be carried on any suitable carrier.

The meter 2 includes circuitry for interrogating the Container RFID tag, the Patient RFID tag and the Operator RFID tag, and for reading and storing data from those tags. Suitable circuitry for these purposes will be well known to those skilled in the art of electronics.

When a blood glucose reading is to be taken, the operator performs the following steps. With the meter 2 switched on, a test strip 16 is taken from its container 10 and inserted into the slot 8 in the meter 2 so that the electrode contacts 18 make contact with corresponding contacts (not shown) within the meter 2. This action activates the meter to expect a glucose reading to be taken within a predetermined time, and polarises the working electrode on the test strip 16. The meter prompts the operator to input data from the Container RFID tag 14, the Patient RFID tag 2B and from the Operator RFID tag 32. The meter may specify an order for these actions to be carried out or it may be programmed to accept the input data in any order. After each tag has been accessed, the meter beeps or flashes an LED 5 to indicate a successful download. The graphic display 4 also shows when a download has been successful and prompts the operator to take a reading when all inputs have been received. If a test strip 16 is indicated to be beyond Its shelf life (open-container or closed-container date) an alarm condition is triggered and the meter 2 prompts the operator to discard the container 10 and remaining test strips 16. The meter 2 also prompts the user to open a new container and swipe the meter 2 against the new container to download the data in the new Container RFID tag. The meter 2 may be programmed not to permit a blood glucose reading to be taken until these actions have been carried out within a pre-set time.

Once the meter has verified that all RFID tag information has been downloaded successfully and that the test strip 16 is within its shelf life, the meter prompts the operator to take a blood glucose measurement. This is done in a manner well known per se, by lancing the patient's fingertip or alternative site such as the forearm, to produce a drop of blood which is transferred to the electrodes 20. The blood sample may be applied directly to the electrodes 20, or via a capillary flow path (not shown) in a manner well known in the art. When the electrodes 20 are covered by the blood sample, a current is generated which is proportional to the blood glucose concentration. The meter 2 displays a blood glucose concentration value on the display 4, based on the measured current and on the calibration data downloaded from the Container RFID tag 14. The concentration value is stored in the meter together with the date and time of the reading and associated data from the RFID tags 14, 28, 32. Further readings may be taken and stored in a similar manner. In this example, each time a reading is taken by the meter 2, the meter prompts the operator to swipe the meter against each RFID tag, and the meter can store a plurality of readings for different patients and different operators. Alternatively, it would be possible for the meter to accept the originally-input data as correct until either new data are input or the meter is switched off or put in standby mode, or until a specified time period has elapsed. However, for safety reasons, it is preferred that the meter prompt for each RFID tag to be read before each reading to ensure data integrity.

Figure 6:
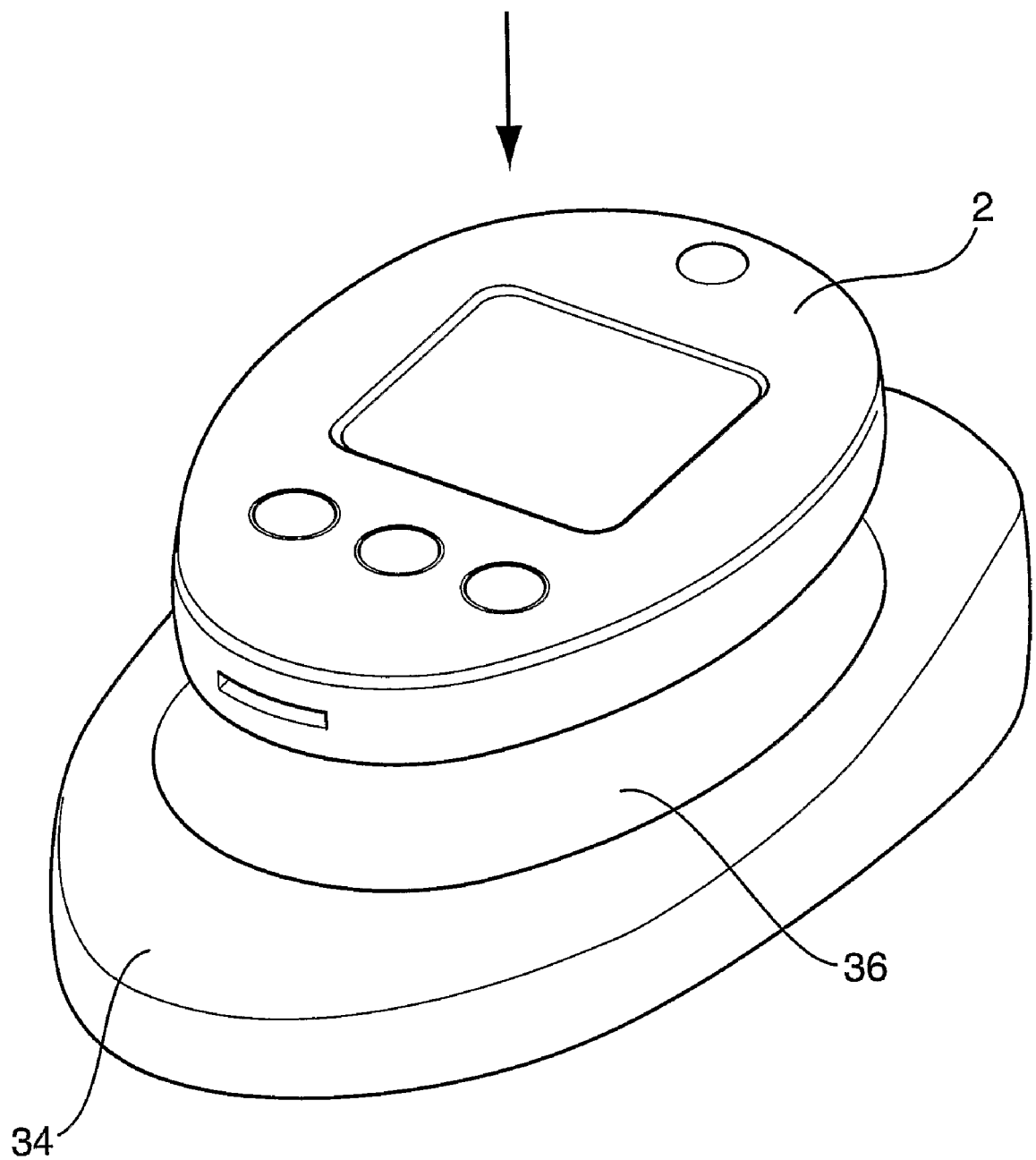
FIG. 6 shows the test meter of FIG. 1 with a reader for reading data from the meter.

At any convenient time, or when the meter's memory is full, the blood glucose readings and their associated data may be transferred to the care facility's computer system. In the embodiment illustrated in FIG. 6, the meter 2 is placed, in a cradle region 36 of a reader 34 which is connected to the computer system (not shown). The reader 34 receives the data by any suitable means, in this example by IR transmission. After confirmation of successful data transfer, the meters memory may be cleared to enable further readings to be taken and stored.

It is appreciated that certain features of the invention, which are for clarity described in the context of separate embodiments, may also be provided in combination in a single embodiment. Conversely, various features of the invention which are, for the sake of brevity, described in the context of a single embodiment, may also be provided separately or in any suitable subcombination.

While the present invention has been described with reference to specific embodiments, it should be understood that modifications and variations of the invention may be constructed without departing from the scope of the Invention defined in the following claims.

The invention claimed is:

1. A test system for measuring the concentration of an analyte in a biological fluid sample, the system comprising:
    a plurality of test members in a container, each test member including reagent means for indicating the catalytic activity of an enzyme when in the presence of a biological fluid containing an analyte acted upon by the enzyme;
    a test meter for receiving a test member, the meter having circuitry for performing a measurement on a test member received therein to produce a measured physical value, means for determining an analyte concentration value for a specified biological fluid from said measured physical value, and means for indicating a determined analyte concentration value;
    a Container RFID tag associated with the container which includes data specific to said plurality of test members; and
    a Patient RFID tag which includes data specific to a patient;
    and wherein said test meter includes means for reading and storing data from said Container RFID tag and from said Patient RFID tag;
    wherein the test meter is programmed to require input from each of said RFID tags before an analyte concentration measurement can be taken; and
    wherein the test meter is programmed to signal an error condition if an analyte concentration measurement has not been made within a pre-set time from reading data from one of the Container RFID tag and the Patient RFID tag.

2. A test system according to claim 1, further comprising an Operator RFID tag to be associated with an operator and which includes operator-specific data; and wherein the test meter includes means for reading and storing data from the Operator RFID tag.

3. A test system according to claim 1, wherein the data readable from the Container RFID tag include calibration data relating to a batch of test members in the container.

4. A test system according to claim 3, wherein the data readable from the Container RFID tag further include data relating to the test members in the container and selected from: the lot number, the date of manufacture of the test members, the shelf life of the test members, and open-date or expiry-date deadlines.

5. A test system according to claim 1, further comprising a reader for receiving analyte concentration value data and associated data from the meter and for transferring said data to a computer database.

6. A test system according to claim 1, wherein the or each RFID tag is passive.

7. A test system according to claim 1, wherein the or each RFID tag must be positioned less than 10 cm from the test meter for the meter to read data therefrom.

8. A test system according to claim 1, wherein the or each RFID tag must be positioned less than 5 cm from the test meter for the meter to read data therefrom.

9. A test system for measuring the concentration of an analyte in a biological fluid sample, the system comprising:
    a plurality of test members in a container, each test member including reagent means for indicating the catalytic activity of an enzyme when in the presence of a biological fluid containing an analyte acted upon by the enzyme;
    a test meter for receiving a test member, the meter having circuitry for performing a measurement on a test member received therein to produce a measured physical value, means for determining an analyte concentration value for a specified biological fluid from said measured physical value, and means for indicating a determined analyte concentration value;
    a Container RFID tag associated with the container which includes data specific to said plurality of test members; and
    a Patient RFID tag to be associated with a patient and which includes data specific to a patient;
    an Operator RFID tag to be associated with an operator and which includes operator-specific data;
    wherein said test meter includes means for reading and storing data from the Container RFID tag, from the Patient RFID tag, and from the Operator RFID tag; and
    wherein the test meter is programmed to require input from each of said RFID tags before an analyte concentration measurement can be taken; and
    wherein the test meter is programmed to signal an error condition if an analyte concentration measurement has not been made within a pre-set time from reading data from one of the Container RFID tag, the Patient RFID tag and the Operator RFID tag.

10. A test system according to claim 9, further comprising a reader for receiving analyte concentration value data and associated data from the meter and for transferring said data to a computer database.

11. A test system according to claim 9, wherein the or each RFID tag is passive.

12. A test system according to claim 9, wherein the or each RFID tag must be positioned less than 10 cm from the test meter for the meter to read data therefrom.

13. A test system according to claim 9, wherein the or each RFID tag must be positioned less than 5 cm from the test meter for the meter to read data therefrom.

* * * * *